(12) United States Patent
Kadykowski et al.

(10) Patent No.: US 8,048,100 B2
(45) Date of Patent: Nov. 1, 2011

(54) BLUNT DISSECTOR FOR SEPARATING BLOOD VESSELS FROM SURROUNDING TISSUE

(75) Inventors: Randal J. Kadykowski, South Lyon, MI (US); Lyne M. Charron-Keller, Brighton, MI (US); Seiji Maeda, Tokyo (JP); Susumu Komagata, Tokyo (JP); Hideyuki Kasahara, Tokyo (JP); Akihito Kano, Tokyo (JP); Ken Yamatani, Tokyo (JP)

(73) Assignee: Terumo Cardiovascular Systems, Corp., Ann Arbor, MI (US)

( * ) Notice: Subject to any disclaimer, the term of this patent is extended or adjusted under 35 U.S.C. 154(b) by 732 days.

(21) Appl. No.: 12/136,477

(22) Filed: Jun. 10, 2008

(65) Prior Publication Data

US 2009/0306699 A1    Dec. 10, 2009

(51) Int. Cl.
*A61B 17/00* (2006.01)
(52) U.S. Cl. ...................................................... 606/190
(58) Field of Classification Search .................. 606/190, 606/151, 159, 170, 171, 180; 600/96–99, 600/104, 114, 210, 201, 207
See application file for complete search history.

(56) References Cited

U.S. PATENT DOCUMENTS

| | | | |
|---|---|---|---|
| 5,702,417 A | 12/1997 | Hermann | |
| 5,782,854 A | 7/1998 | Hermann | |
| 5,893,866 A | 4/1999 | Hermann et al. | |
| 5,895,353 A | 4/1999 | Lunsford et al. | |
| 5,944,734 A | 8/1999 | Hermann et al. | |
| 5,951,584 A | 9/1999 | Hermann | |
| 5,968,065 A | 10/1999 | Chin | |
| 5,976,168 A | 11/1999 | Chin | |
| 5,979,452 A | 11/1999 | Fogarty et al. | |
| 5,980,549 A | 11/1999 | Chin | |
| 5,993,472 A | 11/1999 | Hermann et al. | |
| 6,004,340 A | 12/1999 | Hermann et al. | |
| 6,080,102 A * | 6/2000 | Konou et al. | 600/114 |
| 6,193,653 B1 * | 2/2001 | Evans et al. | 600/210 |
| 6,240,924 B1 | 6/2001 | Fogarty et al. | |
| 6,432,044 B1 | 8/2002 | Lunsford et al. | |
| 6,471,638 B1 | 10/2002 | Chang et al. | |
| 6,596,010 B1 | 7/2003 | Hermann et al. | |
| 6,752,756 B2 | 6/2004 | Lunsford et al. | |
| 6,863,674 B2 | 3/2005 | Kasahara et al. | |
| 6,923,759 B2 | 8/2005 | Kasahara et al. | |
| 6,951,568 B1 | 10/2005 | Chin | |
| 6,958,069 B2 | 10/2005 | Shipp et al. | |
| 7,014,616 B2 | 3/2006 | Ferrera | |
| 7,037,317 B2 | 5/2006 | Hermann et al. | |
| 7,077,803 B2 | 7/2006 | Kasahara et al. | |
| 7,316,683 B2 | 1/2008 | Kasahara et al. | |
| 2003/0130674 A1 | 7/2003 | Kasahara et al. | |
| 2005/0137613 A1 | 6/2005 | Kasahara et al. | |
| 2005/0149094 A1 | 7/2005 | Kasahara et al. | |
| 2006/0058830 A1 | 3/2006 | Hermann et al. | |
| 2006/0173474 A1 | 8/2006 | Wellman et al. | |
| 2006/0211916 A1 | 9/2006 | Kasahara et al. | |
| 2007/0149993 A1 | 6/2007 | Kasahara et al. | |

* cited by examiner

*Primary Examiner* — Kevin T Truong
(74) *Attorney, Agent, or Firm* — Gael Diane Tisack, Esq.; Mark L. Mollon, Esq.; Darryl Newell

(57) ABSTRACT

A blunt dissector for separating a blood vessel from surrounding tissues in a body comprises a longitudinal rod having a proximal end, a distal end, and an internal passage for conducting insufflation gas between the proximal and distal ends. An interior sleeve is mounted within the longitudinal rod for receiving an endoscope at the proximal end. A transparent tip is mounted to the distal end of the longitudinal rod. A handle is mounted to the proximal end of the longitudinal rod. The longitudinal rod has an outer surface along substantially all of the longitudinal rod between the proximal and distal ends consisting essentially of a fluoropolymer.

23 Claims, 5 Drawing Sheets

BLUNT DISSECTOR FOR SEPARATING BLOOD VESSELS FROM SURROUNDING TISSUE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to a tissue separation dissector used for forming an elongated cavity in subcutaneous tissue, particularly along the course of a small blood vessel. More specifically, this invention relates to an endoscope-covering sheath used for endoscopic blood vessel harvesting which endoscopically harvests a subcutaneous blood vessel such as the great saphenous vein.

Surgical methods and endoscopic dissectors for dissecting and harvesting a subcutaneous blood vessel such as a great saphenous vein are known in, for example, U.S. Pat. Nos. 7,077,803; 6,863,674; 6,432,044; and 5,895,353, incorporated by reference in their entirety. The dissector is a straight tubular device with an internal instrument insertion passage and a handle portion provided at the proximal end of the dissector. A rigid endoscope is introduced in the instrument insertion passage of the dissector from the end of the handle portion.

When a subcutaneous blood vessel, such as a great saphenous vein, is to be endoscopically dissected by using the dissector, a surgical method such as demonstrated by FIG. 21 is utilized. The entire length of a target blood vessel C extending from the upper portion of the inguinal region A of the thigh of a lower limb 1000 to the ankle B is desired to be removed. The medical professional (i.e., the operator) performs a skin incision E2 at the knee area D, for example, immediately above the blood vessel C by means of a scalpel or the like. The operator exposes the blood vessel C in the area of the skin incision E2 by means of blunt dissection or the like. The operator parts tissue immediately above the blood vessel C by means of a dissector over a distance from a portion of skin E2 such that the blood vessel is observable to the naked eyes. Once the vessel is fully dissected from the surrounding tissue, small incisions (herein after referred to as stab wounds) are performed distal to the knee incision (e.g., at inguinal position E1 and ankle position E3) and blood vessel C is extracted through incision E2.

FIG. 22 shows a cross-sectional view taken along line 22-22 of FIG. 21. Reference numeral 1001 denotes skin, reference numeral 1002 denotes a subcutaneous tissue, and reference numeral 1003 denotes a connective tissue overlying and surrounding blood vessel C. In a dissecting operation, the operator first uses a dissector rod having a blunt conical tip to form a cavity G between the surrounding tissue and blood vessel C. Blood vessel C is isolated from the surrounding connective tissue 1003 anteriorly, posteriorly, laterally, and medially as much as possible using the dissector rod. Following blunt dissection from connective tissue 1003, blood vessel C continues to be connected to the body of the patient by side branches F of the vessel and by remaining bits of connective tissue.

In order to harvest blood vessel C, the side branches F and remaining connective tissue between the incised portions of skin E2 at knee D and inguinal region A must be removed. Thus, the operator removes the dissector rod and inserts a harvesting tool into cavity G through incised portion of skin E2. The harvester includes a keeper (i.e., loop) for slidably receiving vessel C. The operator progressively slides the tip of the harvester from incision E2 alternately toward the incised portions of skin E1 and E3 along an outer surface of blood vessel C while observing through the rigid endoscope loaded into the interior of the harvester and cutting through side branches F and remaining connective tissue using a cutter (i.e., forceps) that is integral with the keeper. In the course of the cutting operation within cavity G, the operator moves the harvester device back and forth while cutting (e.g., cauterizing) branches by manipulating a set of controls disposed at the proximal end of the harvester. An insufflation gas (e.g., $CO_2$) is introduced into cavity G through the tip of both the dissector rod and the harvester rod to hold open cavity G and maintaining separation between vessel C and the surrounding subcutaneous tissue 1002 and connective tissue 1003.

During initial dissection of cavity G (referred to as the first pass), the dissector encounters high resistance so that the operator must manually apply a strong force to move forward. The resistance is due to the blood vessel C, the connective tissue 1003 and the subcutaneous tissue 1002 being connected tightly together. The prior art has suffered from operator fatigue and inefficient performance of the dissection/harvesting operation.

SUMMARY OF THE INVENTION

In view of the prior state of the art, it would be desirable to reduce operator strain and fatigue and to facilitate an easier and more efficient dissecting operation to overcome the tight connection of the desired blood vessel to surrounding subcutaneous and connective tissues.

In one aspect of the invention, a blunt dissector for separating a blood vessel from surrounding tissues in a body comprises a longitudinal rod having a proximal end, a distal end, and an internal passage for conducting insufflation gas between the proximal and distal ends. An interior sleeve is mounted within the longitudinal rod for receiving an endoscope at the proximal end. A transparent tip is mounted to the distal end of the longitudinal rod. A handle is mounted to the proximal end of the longitudinal rod. The longitudinal rod has an outer surface along substantially all of the longitudinal rod between the proximal and distal ends consisting essentially of a fluoropolymer.

We have found that when the outer surface of the dissector along the longitudinal rod is covered by or consists entirely of fluoropolymer (such as polytetrafluoroethylene), much less force is required during dissection compared to when using a conventional dissector. Moreover, a contoured handle with a flanged shape at the distal portion and a bulb shape at the proximal portion facilitate a more efficient and comfortable application of the necessary force with less likelihood of repetitive stress injury to the user.

DETAILED DESCRIPTION OF PREFERRED EMBODIMENTS

Figure 1:
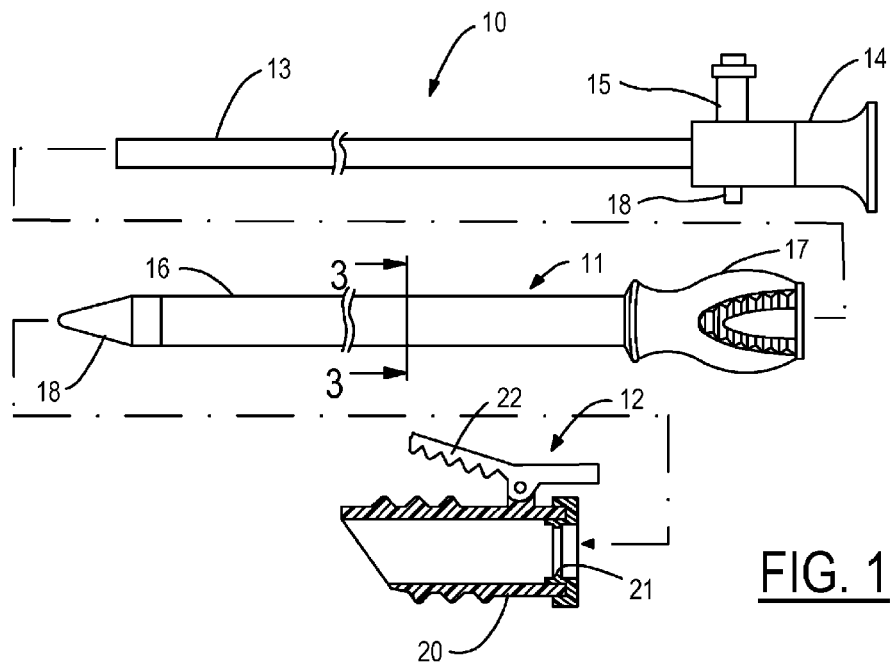
FIG. 1 is a plan view of a blunt dissector of the invention together with an endoscope and a trocar.
Figure 2:
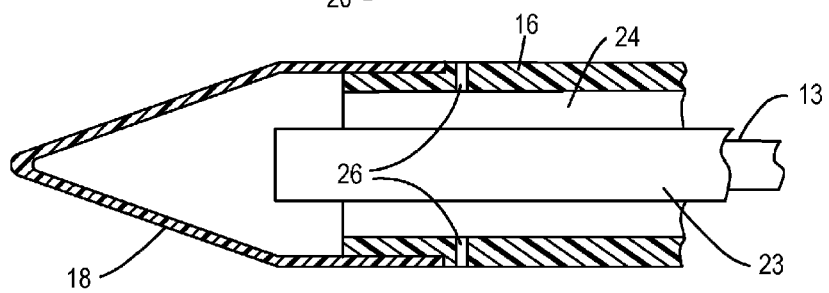
FIG. 2 is a side cross-sectional view of the tip of the dissector.

A dissection system includes an endoscope 10 to perform observation in a body, a dissector apparatus 11 to dissect a blood vessel in the body, and trocar 12 to help insert the endoscope 10 and dissector apparatus 11 into the body. Endoscope 10 is a rigid endoscope and includes an elongated rod-like inserting portion 13. The proximal end of inserting portion 13 connects to an end adapter 14 to transmit an endoscopic image. A light guide port 15 projects from end adapter 14. Light guide port 15 connects to a light guide cable to supply illumination light to the endoscope 10.

In a preferred embodiment, dissector apparatus 11 includes a tubular main body portion 16 comprising a hollow longitudinal rod within which endoscope 10 is to be inserted. Endoscope 10 is inserted or removed from longitudinal rod 16 through a handle portion 17 in one fluid forward or backward movement. Endoscope 10 is secured inside dissector 11 by a small nub 18, found opposite light guide port 15 on end adapter 14 of endoscope 10 and held by a conventional mechanism found inside handle portion 17.

The material of longitudinal rod 16 material is selected from fluoropolymers, which are well known materials. Examples of fluoropolymers include polymers such as polytetrafluoroethylene (PTFE commonly referred to as Teflon), perfluoroalkoxy (PFA), fluorinated ethylene propylene (FEP), polyvinylidene fluoride (PVDF), ethylene-tetrafluoroethylene (ETFE), ethylene-chlorotrifluoroethylene (ECTFE), and mixtures of fluoropolymers such as MFA or THV, or mixtures of any of the foregoing. The most preferred material for constituting the outer surface of longitudinal rod 16 is PTFE. The use of a fluoropolymer reduces the friction caused by moving rod 16 through connective tissue, thereby reducing the force required to perform a dissection.

A dissector tip 18 to dissect a blood vessel is disposed at the distal end of longitudinal rod 16. Trocar 12 includes a body 20 to guide dissector apparatus 11 into the incision site. An aperture seal 21 is located on the surface of the proximal end of body 20. Aperture seal 21 allows dissector 11 to be inserted in body 20 of trocar 12 in one fluid forward motion. The outer surface of trocar body 20 includes a projection to engage with living tissue and a holding portion 22 to hold the body 20 onto the living tissue.

Dissector 11 includes an inner sleeve 23 for receiving inserting portion 13 of rigid endoscope 10. Sleeve 23 is disposed at the axial center of longitudinal rod 16 which has a straight cylindrical shape. Tip member 18 has a conical shape and comprises a transparent synthetic resin material. Longitudinal rod 16 has an internal passage 24 for conducting insufflation gas between the proximal and distal ends. The proximal end of passage 24 communicates with a gas supply (not shown). At its distal end, passage 24 communicates through a hole 26 in longitudinal rod 16 with the body cavity being dissected.

Figure 3:
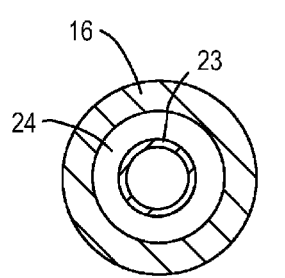
FIGS. 3-6 are longitudinal cross sections for three separate embodiments of the invention.

FIG. 3 shows a cross section of a first embodiment of dissector 11 taken at line 25-25 of FIG. 1. Longitudinal rod 16 consists essentially of a fluoropolymer body shaped as a monolithic cylinder. Preferably, rod 16 may be extruded in the shape of a cylinder. Other extruded shapes are also possible, and may include ribs or bores. Sleeve 23 is also cylindrical and is preferably formed of a metal, such as stainless steel. Sleeve 23 is suspended from a mounting block (not shown) within handle 17 to keep it concentrically spaced from longitudinal rod 16. The space established between sleeve 23 and rod 16 creates passage 24.

Figure 4:
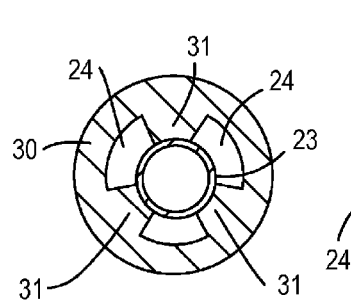
Figure 5:
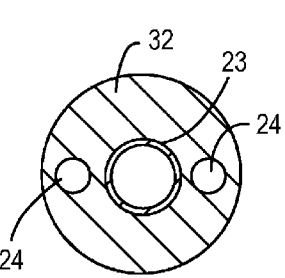

FIG. 4 shows a cross section of a second embodiment of dissector 11 taken at line 25-25 of FIG. 1. Longitudinal rod 30 has a cylindrical shape to which longitudinal ribs 31 are added in order to directly support inner sleeve 23. Passage 24 is thus formed between longitudinal ribs 31. FIG. 5 shows another alternative embodiment wherein the thickness of longitudinal rod 32 is increased so that it supports inner sleeve 23 all the way around its perimeter. A pair of longitudinal bores run between the proximal and distal ends of rod 32 to provide insufflation passage 24.

Figure 6:
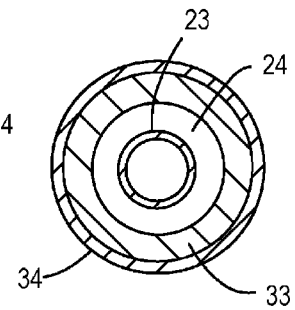

FIG. 6 shows a fourth embodiment similar to the first embodiment, except that the longitudinal rod is a composite structure having a metal cylinder 33 with an outer coating 34 comprised of a fluoropolymer.

The typical manner of using the dissector will be discussed with reference to FIGS. 7-9 which show an operation of harvesting a blood vessel 40 such as a saphenous vein of a lower limb 41 (FIG. 7) or a subcutaneous vessel of an upper limb 42 (FIG. 8) to use the harvested blood vessel 40 for cardiac bypass surgery. When harvesting blood vessel 40, it must be dissected from connective tissue 43.

To initiate the operation, an incision 44 is made in the vicinity of a knee 45 or wrist 46 immediately above blood vessel 40 to be harvested. Body 20 of trocar 12 is inserted in the incision and held by holding portion 22 with respect to the incision. Endoscope 10 is inserted in dissector apparatus 11. Light guide connector 15 of endoscope 10 is inserted in dissector 11. Small nub 18 located on the bottom portion of endoscope 10 engages a mechanism in handle 17 to lock them. The distal end of endoscope 10 is caused to project from the distal end of longitudinal rod 16 into tip 18 for providing a view through tip 18. Endoscope 10 and dissector 11 are then inserted into the body through trocar 12 in one forward movement.

Figure 7:
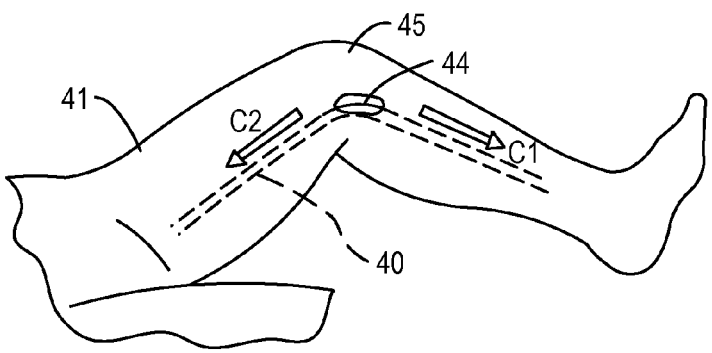
FIG. 7 illustrates the surgical procedure for harvesting a vessel from the leg of a patient.
Figure 8:
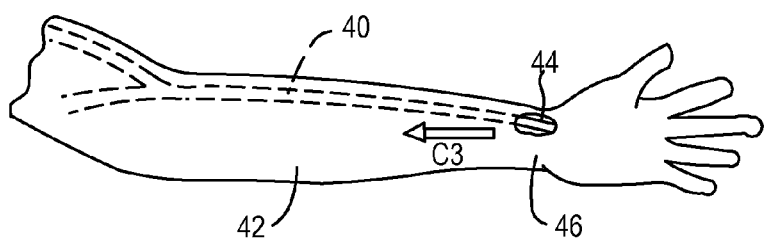
FIG. 8 illustrates the surgical procedure for harvesting a vessel from the arm of a patient.
Figure 9:
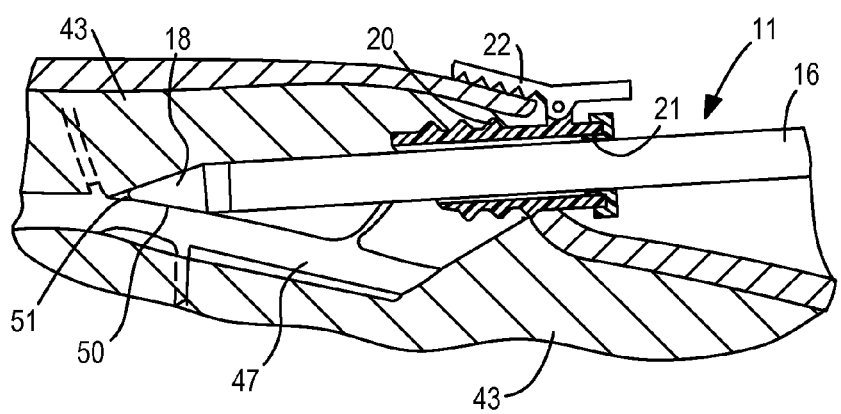
FIG. 9 is a partial cross section showing a dissector inserted into a patient's body and guided by a trocar.

As indicated by arrows C1, C2, and C3 in FIGS. 7 and 8, dissector 11 inserted in the body dissects a main duct 47 of vessel 40 from connective tissue 43 as seen in FIG. 9. More specifically, by manipulating dissector 11, tip 18 is arranged such that one flat side 50 faces main duct 47. Consequently, main duct 47 extends from a periphery to the center in the observed image from endoscope 10. With flat portion 50 being pressed against main duct 47, tip 18 is moved forward along main duct 47 and acute-angled shape 51 at the distal end of tip 18 is inserted between blood vessel connective tissue 43 and main duct 47 in order to progress the dissection.

Figure 10:
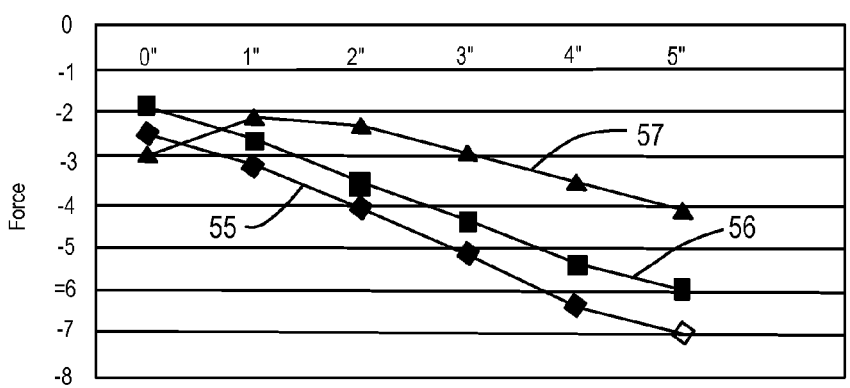
FIG. 10 is a graph showing the force required for penetrating a body with a dissector of the present invention and two prior art dissectors.

As is apparent from FIG. 9, the outer surface of longitudinal rod 16 slides against increasing amounts of connective tissue 43 as the dissection progresses. The inventors have determined that friction between them significantly increases the force required to maintain the reciprocating motions involved in the dissection process. However, the use of a fluoropolymer at the outer surface of rod 16 substantially reduces the friction, thereby reducing the force required to be applied by the person performing the dissection. FIG. 10 compares test measurements from a simulation wherein a ballistic gel was used to simulate connective tissue. Line 55 represents a dissector of the present invention with a fluoropolymer outer surface for the longitudinal rod. Lines 56 and 57 represent conventional dissectors including a stainless steel rod. At a depth beyond the introduction of the tip, it can be seen that line 55 corresponding to the present invention requires less force to move through the simulated tissue.

A further feature of the invention relates to an improved handle through which an operator applies the necessary force to the dissector rod and tip. Thus, a handle 60 includes a flange section 61 at the distal end, a neck section 62, and a bulb section 63 at the proximal end. A camera head cable 64 is connected to a camera head 65 that is coupled to an eyepiece unit 66 of an endoscope. The other end of camera head cable 64 is connected to a central processing unit (CPU) and monitor 67. A light guide cable 68 is connected to a light guide port 70 of the endoscope near eyepiece unit 66, and the other end of light guide cable 68 is coupled to a light source apparatus 71.

Figure 11:
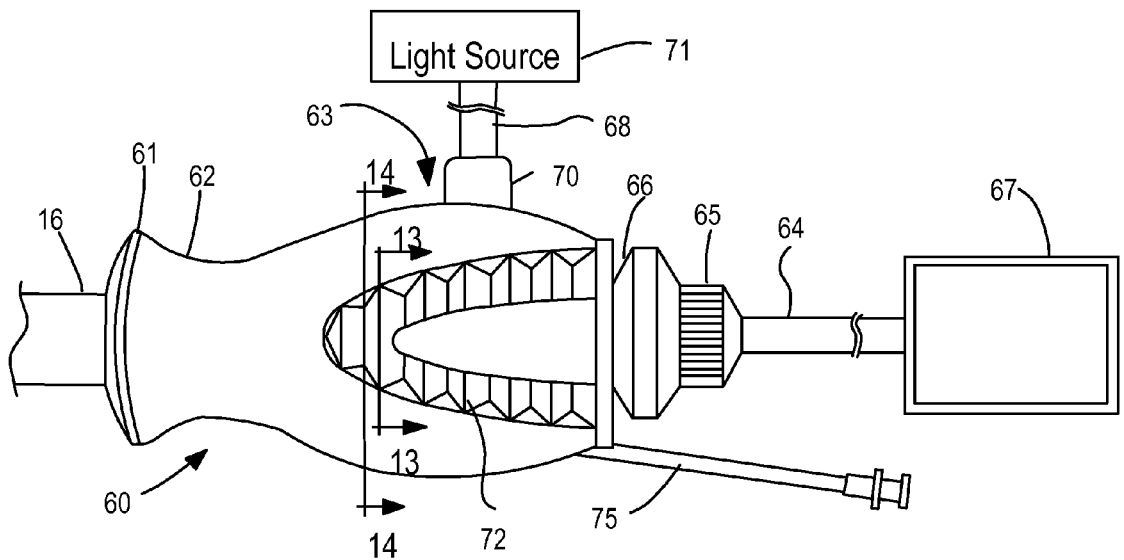
FIG. 11 is a side view showing one embodiment of a handle of the present invention and associated equipment.
Figure 12:
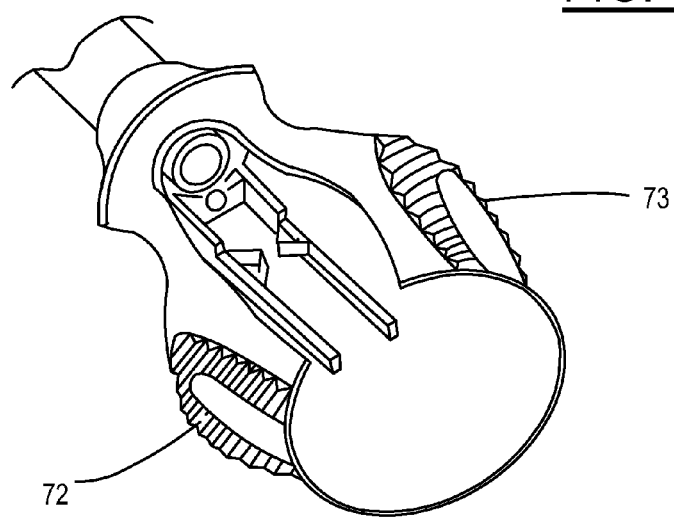
FIG. 12 is a perspective view of the handle of FIG. 11.
Figures 13, 14:
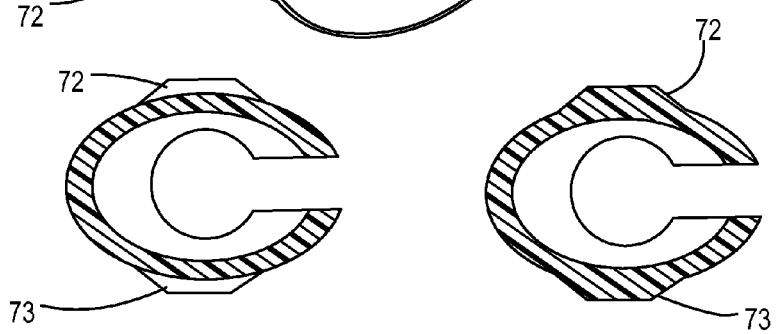
FIG. 13 is a longitudinal cross section along line A-A of FIG. 11.
FIG. 14 is a longitudinal cross section along line B-B of FIG. 11.

The arrangement having a bulb section 63 for being gripped by the palm and last three fingers spaced from a flange section 61 with an intervening neck section 62 with a reduced diameter with respect to the bulb and flange sections, wherein the thumb and index finger grasp in or near neck section 62, results in an improved grip that allows for comfortable application of forces and prevention of unexpected slipping of the hand during dissection. Bulb section 63 includes a pair of arcs 72 and 73 comprising raised surface ridges extending substantially parallel to neck section 62. The surface ridges reduce slippage of the operators hand along handle 60. The profiles of the surface ridges are shown by the cross-sectional views of FIGS. 13 and 14 taken along lines A-A and B-B of FIG. 11, respectively.

The presence of flange section 61 acts to reduce the force required from the operator because it more efficiently transfers the pushing force to the dissector rod and tip. Handle 60 provides maximum comfort and ergonomics while reducing potential for procedure-related physical complications such as carpal tunnel syndrome.

A gas insufflation tubing member 75 is integrated with handle 60 for connecting to a gas supply (not shown). Gas is guided from the supply through gas insufflation tubing member 75, the passageway located inside the dissector, and the hole in the dissector tip to the body cavity being created in order to keep the operation site open and visible. The preferred gas is carbon dioxide ($CO_2$). A convenient length of flexible tubing is provided for gas insufflation tubing member 75. The preferable location of tubing member 75 is away from the gripping sections.

Figure 15:
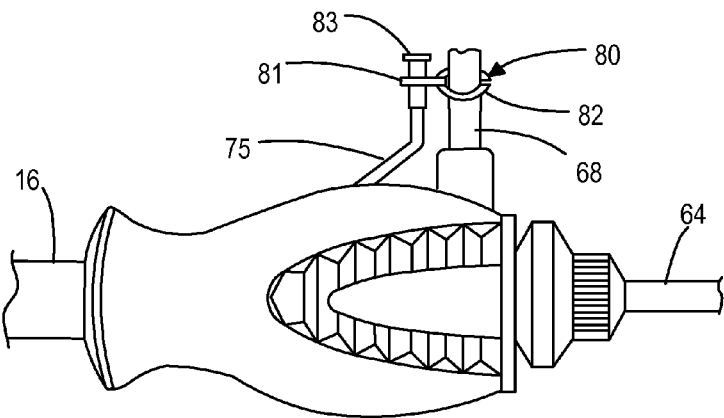
FIGS. 15 and 16 are plan views showing an insufflation tube clipped to various parts of the endoscope.
Figure 16:
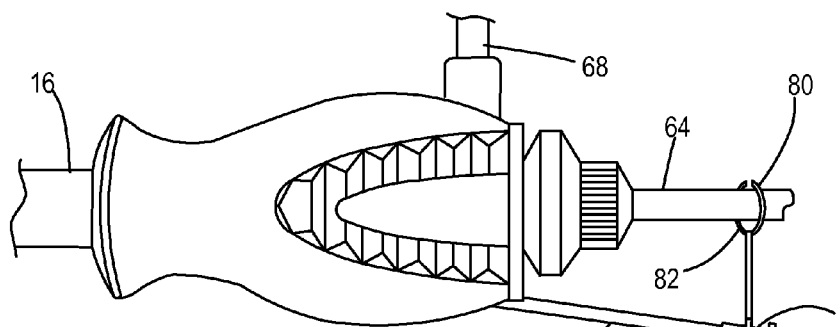

Because a certain amount of slack tubing must be provided for gas insufflation tubing member 75, it may tangle with the user's hand and may interrupt the operation. Tangling may also cause the required gas volume to not be delivered to the distal end of the dissector correctly if tubing member 75 is bent or kinked, obstructing the gas delivery. To solve those problems, a small clip 80 is attached to the end of tubing member 75 as shown in FIGS. 15 and 16. Thus, clip 80 has a first fastener 81 mounted to tubing member 75 (or to an end fitting 83 that may conventionally be provided on tubing member 75). The other end of small clip 80 provides a second fastener that is slidably attached to a portion of the endoscope (e.g., either the light guide cable or the camera head cable). In FIG. 15, the second fastener is attached to light guide cable 68. In FIG. 16, the second fastener is attached to camera head cable 64. The presence of small clip 80 optimizes insufflation tube management during surgery. Preferably, clip 80 is constructed so that the tubing member and the endoscope will be released from each other if an unusual amount of force is applied to either fastener. This protects the endoscope from accidental damage.

Figure 17:
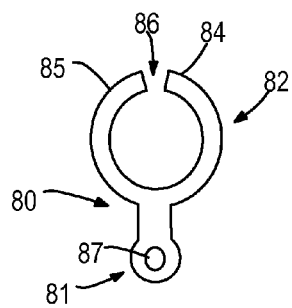
FIGS. 17-21 are plan views showing alternative shapes for the clip of FIGS. 15 and 16.

FIG. 17 shows clip 80 in greater detail. First fastener 81 has an aperture 87 into which the insufflation tube can be mounted. Second fastener 82 has resilient fingers 84 and 85 separated by a gap 86, wherein gap 86 is smaller than the outside diameter of the endoscope light guide cable or the camera head cable. Fingers 84 and 85 can be spread apart by an amount sufficient to insert the desired cable. Clip 80 can be molded rubber, plastic, or a stamped metal piece, for example.

Figure 18:
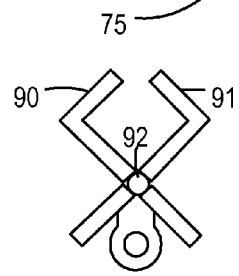

FIG. 18 shows an alternative embodiment wherein the second fastener of clip 80 comprises a movable jaw with a first jaw member 90 and a second jaw member 91 mounted to a pivot 92. A spring (not shown) urges jaw members 90 and 91 into the closed position shown in FIG. 18.

Figure 19:
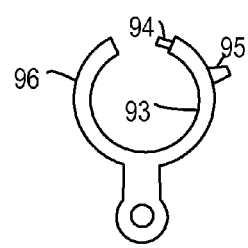

FIG. 19 shows another alternative embodiment wherein a curved finger 93 is hollow to receive a curved pin 94 to form a clasp. Pin 94 slides within finger 93 by pushing on an extension 95 of pin 94. Pin 94 is retracted into the hollow in order to place the endoscope cable within the clip, and then pin 94 is extended toward curved finger 96 so that the cable is retained.

Figure 20:
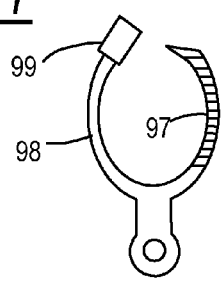

FIG. 20 shows yet another embodiment wherein the second fastener includes bendable fingers 97 and 98. A collar 99 is mounted to the end of finger 98 and has an open end for receiving finger 97 to form a clasp.

Figure 21:
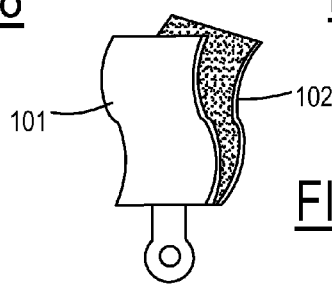
Figure 22:
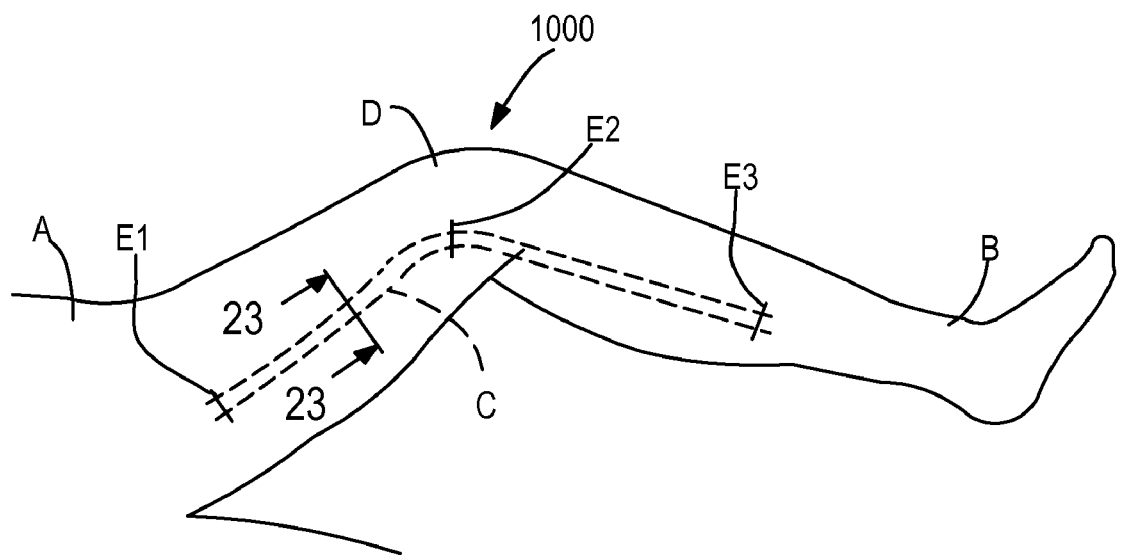
FIGS. 22 and 23 illustrate a prior art vessel harvesting procedure.
Figure 23:
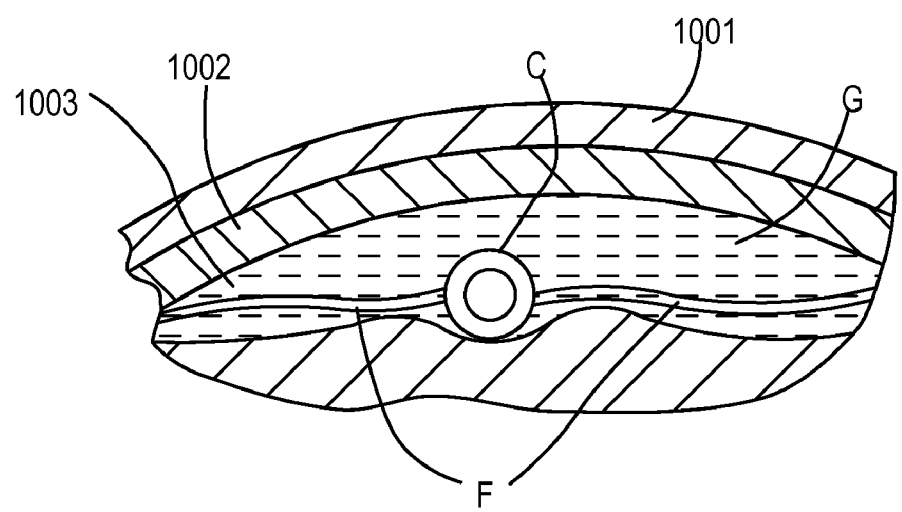

FIG. 21 shows another alternative wherein the second fastener is formed by sheets 101 and 102 having respective hook and loop surfaces. The clip is installed by pulling sheets 101 and 102 apart, passing them around a portion of the endoscope (e.g., the light guide cable or the camera head cable), and joining them back together.

What is claimed is:

1. A blunt dissector for separating a blood vessel from surrounding tissues in a body, comprising:
   a longitudinal rod having a proximal end, a distal end, and an internal passage for conducting insufflation gas between the proximal and distal ends;
   an interior sleeve mounted within the longitudinal rod for receiving an endoscope at the proximal end;
   a transparent tip mounted to the distal end of the longitudinal rod to separate the blood vessel from the surrounding tissues in advance of the longitudinal rod; and
   a handle mounted to the proximal end of the longitudinal rod;
   wherein the longitudinal rod has an outer surface along substantially all of the longitudinal rod between the proximal and distal ends for slidably contacting the surrounding tissues after they have been separated by the transparent tip, the outer surface consisting essentially of a fluoropolymer.

2. The dissector of claim 1 wherein the fluoropolymer is selected from the group consisting of polytetrafluoroethylene (PTFE), perfluoroalkoxy (PFA), fluorinated ethylene propylene (FEP), polyvinylidene fluoride (PVDF), ethylene-tetrafluoroethylene (ETFE), ethylene-chlorotrifluoroethylene (ECTFE), and mixtures thereof.

3. The dissector of claim 1 wherein the fluoropolymer is polytetrafluoroethylene (PTFE).

4. The dissector of claim 1 wherein the outer surface comprises a coating over a support tube comprising a metal.

5. The dissector of claim 1 wherein the longitudinal rod consists essentially of the fluoropolymer.

6. The dissector of claim 5 wherein the longitudinal rod is formed by extruding the fluoropolymer in the shape of a cylinder.

7. The dissector of claim 6 wherein the fluoropolymer is polytetrafluoroethylene (PTFE).

8. The dissector of claim 1 wherein the handle comprises a contoured grip having a bulb section at a proximal end thereof, a flange section at a distal end thereof, and a reduced-diameter neck section therebetween.

9. The dissector of claim 8 wherein the bulb section includes surface ridges extending substantially parallel to the neck section.

10. The dissector of claim 8 wherein the handle comprises resilient material.

11. The dissector of claim 1 further comprising:
a flexible tubing member connected at one end to the internal passage and adapted at the other end to be connected to a gas supply; and
a clip having a first fastener mounted to the flexible tubing member at a substantially fixed location and having a second fastener for slidably grasping a portion of the endoscope.

12. The dissector of claim 11 wherein the portion of the endoscope is comprised of a cable.

13. The dissector of claim 11 wherein the second fastener comprises a pair of resilient fingers.

14. The dissector of claim 11 wherein the second fastener includes a clasp.

15. The dissector of claim 11 wherein the second fastener includes hook and loop sheets.

16. A blunt dissector for separating a blood vessel from surrounding tissues in a body, comprising:
a longitudinal rod having a proximal end, a distal end, and an internal passage for conducting insufflation gas between the proximal and distal ends;
an interior sleeve mounted within the longitudinal rod for receiving an endoscope at the proximal end;
a transparent tip mounted to the distal end of the longitudinal rod to separate the blood vessel from the surrounding tissues in advance of the longitudinal rod; and
a handle mounted to the proximal end of the longitudinal rod, wherein the handle comprises a contoured grip having a bulb section at a proximal end thereof, a flange section at a distal end thereof, and a reduced-diameter neck section therebetween;
wherein the longitudinal rod has an outer cylinder for slidably contacting the surrounding tissues after being separated by the transparent tip, the outer cylinder consisting essentially of polytetrafluoroethylene (PTFE) to provide a PTFE outer surface along substantially all of the longitudinal rod between the proximal and distal ends.

17. The dissector of claim 16 wherein the longitudinal rod is formed by extruding the PTFE in the shape of a cylinder, wherein the handle comprises resilient material, and wherein the bulb section includes surface ridges extending substantially parallel to the neck section.

18. The dissector of claim 16 further comprising:
a flexible tubing member connected at one end to the internal passage and adapted at the other end to be connected to a gas supply; and
a clip having a first fastener mounted to the flexible tubing member at a substantially fixed location and having a second fastener for slidably grasping a portion of the endoscope.

19. A blunt dissector for separating a blood vessel from surrounding tissues in a body, comprising:
a longitudinal rod having a proximal end, a distal end, and an internal passage for conducting insufflation gas between the proximal and distal ends;
an interior sleeve mounted within the longitudinal rod for receiving an endoscope at the proximal end;
a transparent tip mounted to the distal end of the longitudinal rod; and
a handle mounted to the proximal end of the longitudinal rod;
a flexible tubing member connected at one end to the internal passage and adapted at the other end to be connected to an insufflation gas supply;
a clip having a first fastener mounted to the flexible tubing member at a substantially fixed location and having a second fastener for slidably grasping a portion of the endoscope.

20. The dissector of claim 19 wherein the portion of the endoscope is comprised of a cable.

21. The dissector of claim 19 wherein the second fastener comprises a pair of resilient fingers.

22. The dissector of claim 19 wherein the second fastener includes a clasp.

23. The dissector of claim 19 wherein the second fastener includes hook and loop sheets.

* * * * *